US012678331B2

(12) United States Patent
Gerlach

(10) Patent No.: US 12,678,331 B2
(45) Date of Patent: Jul. 14, 2026

(54) APPARATUS AND METHOD FOR LENS SURGERY

(71) Applicant: Carl Zeiss Meditec AG, Jena (DE)

(72) Inventor: Mario Gerlach, Glienicke-Nordbahn (DE)

(73) Assignee: Carl Zeiss Meditec AG, Jena (DE)

( * ) Notice: Subject to any disclaimer, the term of this patent is extended or adjusted under 35 U.S.C. 154(b) by 558 days.

(21) Appl. No.: 17/767,960

(22) PCT Filed: Oct. 9, 2020

(86) PCT No.: PCT/EP2020/078403
§ 371 (c)(1),
(2) Date: Apr. 11, 2022

(87) PCT Pub. No.: WO2021/069658
PCT Pub. Date: Apr. 15, 2021

(65) Prior Publication Data
US 2024/0091065 A1      Mar. 21, 2024

(30) Foreign Application Priority Data

Oct. 10, 2019    (DE) .......................... 102019127343.9

(51) Int. Cl.
*A61F 9/008*          (2006.01)
(52) U.S. Cl.
CPC ..................... *A61F 9/00834* (2013.01); *A61F 2009/00844* (2013.01); *A61F 2009/0087* (2013.01); *A61F 2009/00872* (2013.01)

(58) Field of Classification Search
None
See application file for complete search history.

(56) References Cited

U.S. PATENT DOCUMENTS

| | | | |
|---|---|---|---|
| 3,991,426 | A | 11/1976 | Flom et al. |
| 4,166,293 | A | 9/1979 | Anis |
| 4,177,526 | A | 12/1979 | Kuppinger et al. |

(Continued)

FOREIGN PATENT DOCUMENTS

| | | |
|---|---|---|
| AU | 2004202852 A1 | 7/2004 |
| CA | 3 002 085 A1 | 5/2017 |

(Continued)

*Primary Examiner* — Michael T. Holtzclaw
(74) *Attorney, Agent, or Firm* — Christensen, Fonder, Dardi & Busse PLLC; John P. Fonder

(57)          ABSTRACT

An apparatus for refractive lens surgery on the human eye, including: a laser device for separating tissue of the eye lens and capsular bag in a focus of pulsed laser radiation, a focus positioning device for setting and adjusting a location of the focus, a measuring apparatus for gathering the relative position of the eye lens and capsular bag, and a control device which reads data from the measuring apparatus and controls the focus positioning device, and which is designed to define and specify a pattern for the focus to the focus positioning device, the pattern separating tissue layers in the eye lens for the purposes of generating an accommodation space for an intralenticular intraocular lens. The accommodation space includes a cutout for a dimensionally-stable lens body of the intraocular lens and a peripheral fastening region for fixing the dimensionally-stable lens body at a single, predetermined, axial position.

15 Claims, 15 Drawing Sheets

(56)                References Cited

U.S. PATENT DOCUMENTS

| | | | |
|---|---|---|---|
| 4,242,761 A | | 1/1981 | Chase et al. |
| 4,244,060 A * | | 1/1981 | Hoffer .................. A61F 2/16015 |
| | | | 623/6.15 |
| 4,268,921 A | | 5/1981 | Kelman |
| 5,066,301 A | | 11/1991 | Wiley |
| 5,443,506 A | | 8/1995 | Garabet |
| 5,728,155 A | | 3/1998 | Anello et al. |
| 6,007,579 A | | 12/1999 | Lipshitz et al. |
| 8,303,656 B2 * | | 11/2012 | Shadduck ............. A61F 2/1635 |
| | | | 623/6.22 |
| 9,095,424 B2 | | 8/2015 | Kahook et al. |
| 2002/0002404 A1 | | 1/2002 | Sarfarazi |
| 2002/0128710 A1 | | 9/2002 | Eggleston |
| 2002/0143394 A1 | | 10/2002 | Lang |
| 2003/0158560 A1 | | 8/2003 | Portney |
| 2006/0100612 A1 | | 5/2006 | van der Heyd et al. |
| 2007/0010881 A1 | | 1/2007 | Soye et al. |
| 2007/0244561 A1 | | 10/2007 | Ben Nun |
| 2008/0039937 A1 | | 2/2008 | Obrebski |
| 2008/0183289 A1 | | 7/2008 | Werblin |
| 2009/0018652 A1 | | 1/2009 | Hermans et al. |
| 2010/0191230 A1 | | 7/2010 | Dick et al. |
| 2010/0204787 A1 | | 8/2010 | Noy |
| 2010/0312231 A1 | | 12/2010 | Singh |
| 2010/0324542 A1 * | | 12/2010 | Kurtz .................. A61F 9/00825 |
| | | | 606/6 |
| 2011/0040378 A1 | | 2/2011 | Werblin |
| 2011/0196350 A1 * | | 8/2011 | Friedman ................ A61F 9/008 |
| | | | 606/6 |
| 2013/0190868 A1 * | | 7/2013 | Kahook ................ A61F 2/1635 |
| | | | 623/6.38 |
| 2014/0128731 A1 | | 5/2014 | Gonzalez et al. |
| 2015/0265398 A1 * | | 9/2015 | Hartkens ............. A61F 9/00821 |
| | | | 606/4 |
| 2016/0058553 A1 * | | 3/2016 | Salahieh ............... A61F 2/1629 |
| | | | 623/6.13 |
| 2016/0331520 A1 * | | 11/2016 | Beer .................... A61F 2/1629 |
| 2018/0271645 A1 | | 9/2018 | Brady et al. |
| 2018/0368974 A1 | | 12/2018 | Kahook et al. |
| 2019/0076241 A1 * | | 3/2019 | Alarcon Heredia .. A61F 2/1624 |
| 2019/0290487 A1 | | 9/2019 | Ho et al. |
| 2020/0113736 A1 | | 4/2020 | Bos et al. |

FOREIGN PATENT DOCUMENTS

| | | | | |
|---|---|---|---|---|
| CA | 3 055 996 A1 | 9/2018 | | |
| DE | 26 05 847 A1 | 8/1976 | | |
| DE | 27 25 219 A1 | 12/1978 | | |
| DE | 29 45 349 A1 | 5/1981 | | |
| DE | 31 30 278 A1 | 2/1983 | | |
| DE | 101 05 080 A1 | 8/2002 | | |
| DE | 101 34 072 A1 | 2/2003 | | |
| DE | 10 2006 036 800 A1 | 2/2008 | | |
| EP | 3 375 410 A1 | 9/2018 | | |
| ES | 2390860 T3 * | 11/2012 | .......... | A61F 2/1613 |
| JP | 2013-027673 A | 2/2013 | | |
| PT | 2148628 T | 2/2010 | | |
| WO | WO 99/56670 A1 | 11/1999 | | |
| WO | WO 00/21467 A1 | 4/2000 | | |
| WO | WO 2004/017878 A1 | 3/2004 | | |
| WO | WO 2008/077795 A2 | 7/2008 | | |
| WO | WO 2012/054854 A2 | 4/2012 | | |
| WO | WO 2017/096087 A1 | 6/2017 | | |
| WO | WO 2019/048708 A1 | 3/2019 | | |

* cited by examiner

APPARATUS AND METHOD FOR LENS SURGERY

PRIORITY CLAIM

The present application is a National Phase entry of PCT Application No. PCT/EP2020/078403, filed Oct. 9, 2020, which claims priority from German Patent Application 10 2019 127 343.9, filed Oct. 10, 2019, the disclosures of which are hereby incorporated by reference herein in their entirety.

FIELD OF THE INVENTION

The invention relates to an apparatus and a method for lens surgery on the human eye, wherein an intralenticular intraocular lens is used, especially for refractive lens surgery, for example in cataract surgery.

BACKGROUND OF THE INVENTION

The insertion of intraocular lenses is a conventional treatment for the treatment of cataracts. In the process, the eye lens that has been opacified by the cataract is removed and replaced by an implantable intraocular lens. However, the insertion of an intraocular lens may also be necessary for other reasons. Optics concepts which realize presbyopia correction and/or correct an astigmatism have been realized in recent times. As a result, cataract surgery experienced a transformation from the conventional old-age operation to refractive surgery with the object of realizing freedom from spectacles over all viewing distances and with a very high visual quality. The large majority of intraocular eye lenses are implanted in the residual empty remains of the capsular bag. To this end, the anterior capsular bag membrane is opened by capsulorhexis, the natural eye lens is comminuted and removed, and the posterior chamber intraocular lens is inserted into the remaining capsular bag. To generate the required incisions, short pulse lasers, in particular fs short pulse lasers, have been developed in recent years in order to generate the capsulorhexis and realize the access incisions at the front side of the eye and/or the comminution of the eye lens in the opened capsular bag on the basis of lasers and hence "without blades".

So-called posterior chamber intraocular lenses for implantation into the capsular bag comprise holding devices which are known as "haptics" and are fastened to the actual lens body of the intraocular lens in order to correctly fix and position the latter in the capsular bag. Further options for the insertion of an intraocular lens include fixation to the iris. What are known as anterior chamber intraocular lenses are used to this end.

Reference is made to the following documents in respect of known intraocular lenses: U.S. Pat. No. 4,242,761, DE 2605847 A1, U.S. Pat. No. 4,244,060, US 2008/183289, DE 2725219 A1, U.S. Pat. Nos. 4,166,293, 4,177,526 A, DE2945349 A1, U.S. Pat. No. 4,268,921 A, DE 3130278 A1, US 2002/128710 A, DE 10105080 B4, DE 10134072 B4, U.S. Pat. No. 5,728,155 A, US 2007/010881 A, WO 99/56670 A1, WO 00/21467 A1, US 2013/190868 A, U.S. Pat. No. 6,007,579 A, US 2003/158560 A, US 2002/143394 A, US 2007/244561 A, US 2010/204787 A, WO 2012/054854 A2, EP 1667612 A1, U.S. Pat. Nos. 5,443,506 A, 5,066,301, AU 2004/202852 A1, WO 2008/077795 A2, U.S. Pat. No. 9,095,424 B2, WO 2017/096087 A1 and CA 3002085 A1.

The prior art has therefore disclosed both single-part and multi-part intraocular lenses.

A special form of intraocular lens is referred to in WO 2019/048708 A1, specifically an intralenticular intraocular lens. It is distinguished in that it is fastened to residual remains of the eye lens. In this case, the intraocular lens is processed by means of an fs-laser device not described in any more detail, in such a way that a through opening that offers space for the intraocular lens is created in the central region of the eye lens. Only the capsular bag remains posterior to the through opening. By contrast, the eye lens has been removed completely from the through opening. At its outer edge, the accommodation space created in the eye lens has a peripheral fastening region comprising a plurality of axially spaced apart annular grooves. An intraocular lens is inserted in such a way that its haptics engage in one of the annular grooves. As a result of the axially spaced apart annular grooves, the surgeon is able to choose the relative position along the ocular axis from various possibilities.

EP 3375410 A1 and US 2019/0290487 A1 have disclosed the practice of hollowing out the interior of the natural eye lens by means of fs short pulse laser radiation and then filling said interior with a synthetic lens material. DE 102006036800 A1 describes details regarding an ultra short pulse laser device which likewise hollows out an eye lens by means of fs laser radiation, in such a way that the cavity created can be filled with a gel material. In this way, opacified parts of the eye lens should be removed, and the intention is also to restore accommodation capability. Therefore, filling takes place with a liquid gel that is surrounded from all sides by residual tissue of the natural eye lens instead of with an intralenticular intraocular lens that has a dimensionally stable lens body.

In the human eye, the lens separates the anterior chamber from the vitreous humor. The risk of vitreous humor prolapse, that is to say a displacement of the vitreous humor into the anterior chamber, is a problem in lens surgery. Therefore, conventional intraocular lenses have comparatively stable haptics which are provided in the form of arms on the edge of the intraocular lens and which ensure that the inserted intraocular lens withstands a displacement of the vitreous humor to the best possible extent or renders the latter impossible.

The positioning and design of an intraocular lens is of paramount importance for the success of the surgical intervention. For a sufficiently large patient collective, mean refractive results can be adapted by statistical optimization of constants of the intraocular lens, that is to say its optical form. However, the greatest challenge during implantation is the only limited predictability of the refractive result in the individual case, that is to say for the individual patient. The difficulties with the prediction arise primarily from the limited predictability of the stationary post-surgical anterior chamber depth and the centration and tilt of the intraocular lens. The latter is due to the haptics, in particular, which are attached to the lens body and align the latter. Although it is possible to attempt to predict the lens seat as accurately as possible by correlating a plurality of biometry parameters and statistical adaptation, such assumptions do not necessarily apply to the individual patient with their individual anatomical peculiarities and their individual course of healing. If toric intraocular lenses that are used to correct an astigmatism are inserted, the alignment of the anisotropy axis additionally is a further and hence possibly error-afflicted degree of freedom. In this case, there may be deviations on account of measurement errors in the biometry, inaccuracies in the alignment during the surgical intervention, production tolerances, etc., and hence there may be refractive errors and dissatisfied patients. The aforementioned WO 2019/048708 A1 attempts to rectify these problems by virtue of generating the aforementioned plurality of axially spaced apart grooves for receiving haptics of the intralenticular intraocular lens. With this, the surgeon can alter the relative axial position of the intraocular lens during the intervention or in a second intervention by virtue of moving the haptics from one groove to another. Additionally, the document proposes to use the plurality of grooves for the insertion of a plurality of intraocular lenses.

SUMMARY OF THE INVENTION

The invention is based on the object of improving an apparatus and a method for refractive eye surgery, in particular in respect of a more exact and stable positioning of the intraocular lens, by using an intralenticular intraocular lens.

Embodiments include an apparatus for carrying out lens surgery, in particular refractive lens surgery, on the human eye comprises a laser device for separating tissue of the eye lens and capsular bag in a focus of pulsed laser radiation. The laser device emits pulsed laser radiation and focuses the latter into the eye. In this case, pulsed laser radiation and focusing are designed such that tissue of the eye lens and capsular bag is separated. Further, provision is made of a focus positioning device for setting and adjusting a location of the focus. As a result, the apparatus can form a cut surface by adjusting the location of the focus. A registration device is provided in the apparatus and is formed to reference the relative position of the location of the focus in relation to the relative position of the eye structures which comprise the eye lens and the capsular bag. Thus, the position of the focus in relation to the eye structures is known to the apparatus by way of the registration device. A control device of the apparatus reads the data from the registration device and controls the focus positioning device. In this case, it is formed in such a way that it specifies a pattern for the relative position of the focus to the focus positioning device, said pattern forming certain cut surfaces. In the eye lens, the cut surfaces separate tissue layers for the purposes of generating an accommodation space for an intralenticular intraocular lens. The accommodation space has a cutout for a lens body of the intraocular lens and is open toward the anterior chamber in embodiments. Further, the accommodation space realizes at least one of the following features, that is to say it can be embodied in different variants: In a variant a, the accommodation space comprises a peripheral fastening region for fixing the lens body at a single, predetermined axial position. In a variant b, the accommodation space comprises a fastening region for fixing the lens body, accommodation space and fastening region being designed to receive the intraocular lens in sealing fashion so that the anterior chamber of the eye is separated in sealed fashion from rearward portions of the eye. In a variant c, a continuous posterior layer of tissue of the eye lens remains posterior to the cutout provided for the lens body.

An embodiment also includes an apparatus for planning lens surgery on the human eye which comprises an input interface for inputting measurement data indicating a relative position of eye structures comprising the eye lens and the capsular bag. Further, the apparatus comprises a computer device for defining cut surfaces in the eye lens and for determining a pattern of locations of a focus of pulsed laser radiation, the locations being located on the defined cut surfaces. Further, the apparatus comprises an output interface for outputting data representing the pattern of locations at which the pulsed laser radiation should be emitted by an apparatus. Hence, the data are output to the apparatus emitting the pulsed laser radiation. The computer device defines the interfaces in a manner already explained in relation to the apparatus for carrying out lens surgery. The cut surfaces separate tissue layers in the eye lens for the purposes of generating an accommodation space with the aforementioned properties, in particular in one or more of variants a to b.

An embodiment also includes a method for preparing lens surgery on the human eye, in particular refractive lens surgery, which comprises a plurality of steps: gathering the relative position of measurement data which indicate a relative position of eye structures comprising the eye lens and the capsular bag, defining cut surfaces in the eye lens and determining a pattern of locations of a focus of pulsed laser radiation, the locations being located on the defined cut surfaces, and generating data representing the pattern of locations for an apparatus that emits the pulsed laser radiation. The cut surfaces separate tissue layers in the eye lens for the purposes of generating an accommodation space with the properties already mentioned above for the apparatuses, in particular with the features of one or more of variants a to c.

An embodiment also includes a method for lens surgery on the human eye which comprises the provision of an intralenticular intraocular lens comprising a lens body, the generation of cut surfaces in the eye lens, the cut surfaces separating tissue layers in the eye lens for the purposes of generating an accommodation space with the aforementioned properties, and the removal of a volume delimited by the cut surfaces. Optionally, the method also comprises the insertion of the intraocular lens into the accommodation space.

Variants a to c of the apparatus for carrying out lens surgery, the apparatus for planning lens surgery and the method for preparing lens surgery or carrying out lens surgery have many advantages. One of the most substantial advantages is that the relative axial position of the lens body is precisely defined by each variant on its own or by any combination of the variants and cannot be influenced by the vitreous humor. In particular, there is no need for special haptics which brace the lens body against a possible vitreous humor prolapse. The relative axial position of the lens body is precisely defined by the accommodation space and hence, ultimately, by the defined cut surfaces. In the lead up to the intervention, the cut surfaces are defined in order to place the accommodation space axially (and naturally also laterally) to precisely the location required for the desired optical correction. Therefore, a development for the apparatus in which a measuring device is additionally also present is preferred, said measuring device measuring the eye such that the definition of the accommodation space is derivable from the measurement data. Analogously, such a measuring apparatus is used in the method. The measuring apparatus need not necessarily be used directly during the intervention; instead, it may also be kept available as independent equipment such that the measurement is carried out prior to the surgical intervention. The registration device is provided to be able to ensure the accurate relative position of the cut surfaces in terms of the position, form and size, as defined following the measurement. It references the relative position of the location at which the cut surface is generated by means of the pulsed laser radiation, in relation to the relative position of eye structures comprising the eye lens and the capsular bag. This referencing renders the measurement of the eye independent of the surgical intervention itself, in terms of time, space and equipment. In particular, registering the measuring beam of the measuring device with the processing beam of the pulsed laser radiation using optical means, as provided elsewhere to date in the prior art, is no longer necessary. By way of example, until now, these two beams have been guided over the same scanner and the same lens in the prior art. Since reference is now made to the relative position of eye structures, optical coupling of measuring device and treatment device is no longer necessary. Rather, it is sufficient for the measuring device to render the relative position of optical eye structures likewise captured by the registration device identifiable in the measurement data so that there is referencing to the structures of the eye. Possible structures include the iris, structures of the eye front side or in the posterior chamber or structures of the eye lens or capsular bag, or tissue structures connected therewith. Naturally, the measurement and the registration can of course still be carried out with a single device provided this device meets the requirements of the measuring apparatus and the device is integrated into the apparatus for carrying out lens surgery. However, two different apparatuses are preferably used to this end since a device used only for registration can have a substantially simpler design.

Consequently, unlike in WO 2019/048708 A1, a plurality of annular grooves in which haptics of an intraocular lens engage are no longer provided in variants; instead, the peripheral fastening region only still envisages a single axial position and fixes, as a rule, the dimensionally stable lens body. Inaccuracies as a result of haptics thus are avoided. Rather, the single axial position in which the peripheral fastening region directly fixes the dimensionally stable lens body guarantees a fixed and unchanging axial alignment of the dimensionally stable lens body, and hence of the intraocular lens. Therefore, the approach avoids axial variations, which were either unavoidable for the individual patient in the prior art or intended to be compensated in WO 2019/048708 A1 by the provision of a plurality of axially spaced apart attachment grooves. As a result, there is a much more precise alignment of the dimensionally stable lens body of the intraocular lens.

A substantial advantage of embodiments of the realized intralenticular fastening according to variant b is that the accommodation space is designed such that the intraocular lens and, in particular, the dimensionally stable lens body thereof together with the remaining tissue of the eye lens tightly delimit the anterior chamber in relation to portions located anteriorly to the capsular bag.

Since the relative position of the eye lens and capsular bag was gathered precisely by the measuring device, particularly if the measuring apparatus comprises an OCT, the axial position and hence the design of the accommodation space and—if provided—the peripheral fastening region can be predetermined precisely and in patient-individual fashion. Hence, the pattern of the focal locations which ultimately defines the cut surface for the peripheral fastening region should be defined in patient-individual fashion by the control device or within the scope of the method.

According to variant c, a continuous posterior layer of tissue of the eye lens remains posterior to the cutout for the lens body. A first advantage of this configuration is that the relative axial position of the eye lens can be determined even more precisely since a virtually back-side stop remains for the intraocular lens. Secondly, the natural separation between anterior chamber and posterior eye portions is maintained and a vitreous humor prolapse is precluded without requiring haptics to this end.

Moreover, this drastically reduces the risk of what is known as a secondary cataract. This secondary contract may arise if opacification occurs in the remaining posterior capsular bag on account of deposits should the eye lens be removed anterior to the posterior capsular bag. The risk of a secondary cataract can likewise be reduced if the accommodation space is formed in such a way that even the posterior capsular bag is opened by the pattern and consequently can be removed. A particularly preferred configuration of one of the variants a to c provides for an anterior layer of tissue of the eye lens to be left only in a peripheral eye lens region anterior to the accommodation space such that the cutout for the dimensionally stable lens body is open toward the anterior chamber inside of this peripheral eye lens region. In particular, it is then possible to design the accommodation space as an anteriorly open pocket for an intraocular lens consisting only of the dimensionally stable lens body. Then, considered axially, the peripheral fastening region is in the form of an outwardly tapering undercut.

Further, an intraocular lens with a body formed as a lens body throughout is provided, the annular outer edge of which is inserted into the fastening region according to variant a or b. The lens body and/or the edge contact an inner side of the accommodation space in sealing fashion. For example, the edge is inserted into the undercut in order to fasten the intraocular lens overall. Hence, there are no dedicated fastening portions on the intraocular lens any more, firstly realizing simple fastening and secondly realizing a large effective optical region around the optical axis. By way of example, it has no haptics.

In another preferred configuration, the intralenticular intraocular lens is completely surrounded by remaining tissue of the eye lens post insertion. To this end, a tissue layer of the eye lens remains not only posterior to the cutout but also anterior thereof, said tissue layer being continuous as a result with the exception of an access incision that leads to the accommodation space and penetrates the tissue of the eye lens and capsular bag. Firstly, the material of the accommodation space is removed from the interior of the eye lens through this access incision. Secondly, the material for the lens body of the intraocular lens is injected into the accommodation space through the access incision. It cures by polymerization. In this way, the spatial fixation of the intraocular lens is particularly precise and unchanging since the intralenticular intraocular lens is surrounded by the remaining tissue of the eye lens on all sides in the inserted state.

As already mentioned at the outset, the intraocular lens is fastened without conventional haptics, that is to say without the conventional arms. Thus, forming the peripheral fastening region for snap-lock fastening is particularly preferable for all variants. This usually provides for the intraocular lens to be introduced into the fastening region in a first position and then be rotated through a certain angular value about the optical axis or an axis largely parallel to the optical axis such that snap-lock projections are rotated into a corresponding accommodation in the fastening region. Within the scope of snap-lock technology, the peripheral fastening region does not have a rotationally symmetric form but has portions for inserting the snap-locks provided on the intraocular lens and portions in which the snap-locks latch. The transition from the one portion to the other is implemented by a rotation of the intraocular lens about its optical axis or an axis largely parallel thereto. In this context, the term "largely parallel" focuses on a possibly desired tilt of the intraocular lens in relation to the optical axis of the eye or the visual axis of the eye. This may be of the order of ±10°.

Alternatively or in addition, the peripheral fastening region may be formed with a thread structure for screwing in an intraocular lens provided with a corresponding complementary thread structure on the edge of the dimensionally stable lens body of the intraocular lens.

Preferably, the peripheral fastening region is formed with a shoulder adjacent to the snap lock region, for example, the dimensionally stable lens body of the intraocular lens contacting said shoulder in order to ensure the precise alignment. Particularly preferably, this shoulder is conical and designed for contact with a corresponding counter-conical edge of the dimensionally stable lens body. In this way, the axial position of the lens body of the intraocular lens, in particular, is defined very precisely.

To the extent that aspects of an apparatus for refractive lens correction are described below, these aspects naturally apply equally to a method for refractive lens correction, and vice versa. Also, appropriate embodiments of intraocular lenses are provided within the scope of the invention, said intraocular lenses having a design fitting to corresponding structures of embodiments of the peripheral fastening region or the fixation of the intralenticular intraocular lens. As it were, they represent the counterpart to the fastening region or the fixation of the intraocular lens formed on or in the tissue of the eye lens. Moreover, variants a to c can also be combined, that is to say be realized as a+b, a+c, b+c, a+b+c.

It is understood that the features mentioned above and the features still to be explained below can be used not only in the specified combinations but also in other combinations or on their own without departing from the scope of the present invention.

BRIEF DESCRIPTION OF THE DRAWINGS

The invention will be explained in even more detail below on the basis of exemplary embodiments, with reference being made to the appended drawings, which likewise disclose features essential to the invention. These exemplary embodiments are only illustrative and should not be construed as restrictive. For example, a description of an exemplary embodiment with a multiplicity of elements or components should not be construed as meaning that all of these elements or components are necessary for implementation. Rather, other exemplary embodiments can also contain alternative elements and components, fewer elements or components, or additional elements or components. Elements or components of different exemplary embodiments can be combined with one another, unless stated otherwise. Modifications and variations which are described for one of the exemplary embodiments can also be applicable to other exemplary embodiments. In order to avoid repetition, the same elements or corresponding elements in different figures are denoted by the same reference signs and are not explained a number of times. In the figures.

DETAILED DESCRIPTION

Figure 1:
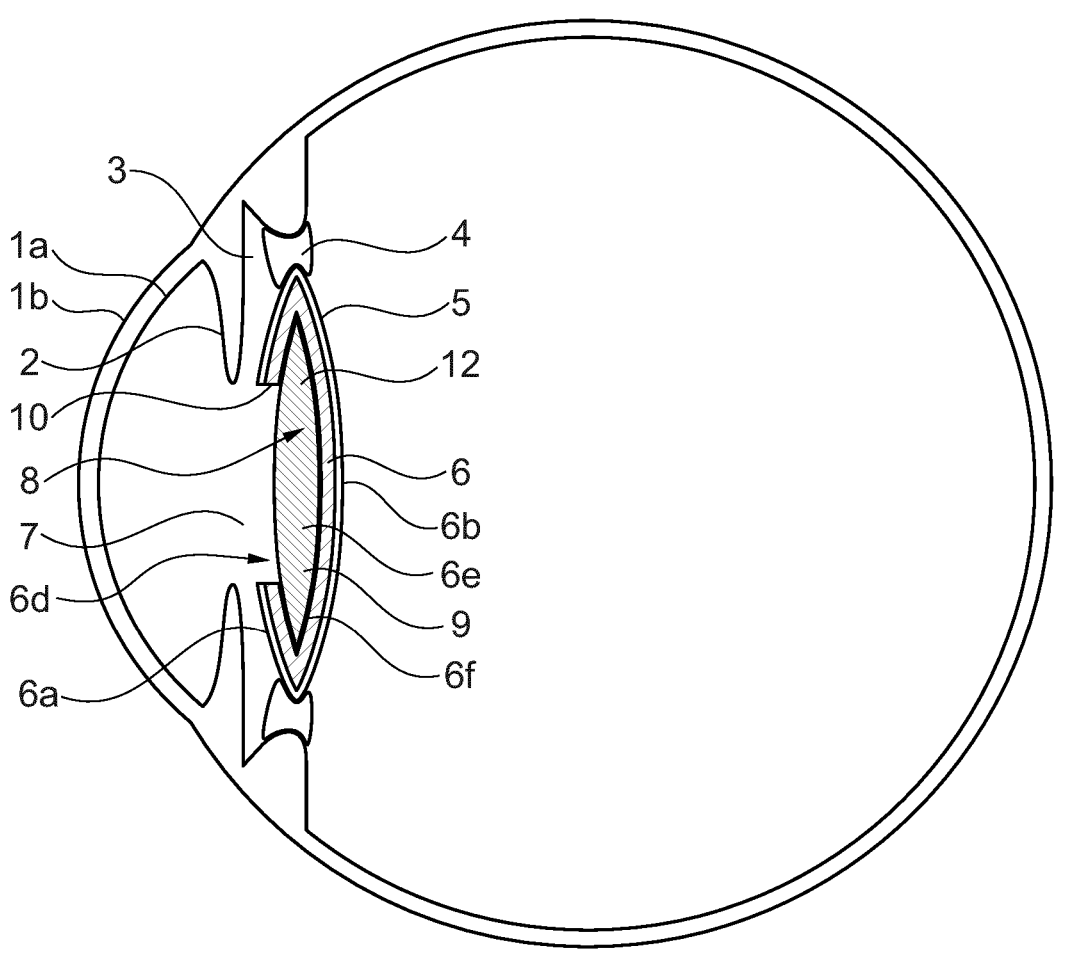
FIG. 1 to 12 show sectional representations through a schematically represented eye with intralenticular intraocular lenses in various embodiments.

FIG. 1 schematically shows a sectional representation through an eye with an intraocular lens inserted into remains of an eye lens. Reference signs of FIG. 1 are likewise used in the further figures for structurally or functionally identical components.

The eye comprises a cornea with a back side 1a facing an anterior chamber 7 of the eye and a front side 1b. The anterior chamber 7 is delimited by the iris 2, which has a sulcus 3 in the region of the posterior chamber. Zonular fibers 4 connect a capsular bag 5 with the remaining eyeball. An eye lens 6 is situated in the capsular bag 5, the capsular bag comprising an anterior capsular membrane 6a and a posterior capsular membrane 6b. A pupil 7 is delimited by the iris 2 and it is well known that there is a retina at the end of the eyeball. In the embodiments described below, an intraocular lens 9 has been inserted into the eye lens 6, for the purposes of which cut surfaces 8 that surround material to be removed are generated in the eye lens 6 by means of a laser processing apparatus, which will still be explained in more detail below on the basis of FIG. 15. This is implemented in such a way that the eye lens 6 provides an accommodation space 6d for the intraocular lens 9. The accommodation space 6d has a cutout 6e for a lens body of the intraocular lens 9 and a fastening region 6f located peripherally thereto.

The material surrounded by the cut surfaces 8 corresponds to those locations in FIG. 1 where the eye lens consisting of widely hatched lens body and capsular bag drawn as a double line is missing. In FIG. 1, this is the accommodation space 6d, which is composed of the volume in which the cutout 6e has been created and the opening access on the front side. As will still be explained below, the cut surfaces 8 are generated by means of laser radiation. They surround the material subsequently removed in order thus to create the accommodation space 6d. In this case, the cut surfaces 8 define the inner surfaces of the accommodation space 6d such that the guidance of the laser beam for generating the cut surface 8 defines the geometry and relative position of the accommodation space 6d. The accommodation space 6d in turn is dimensioned such that it holds the intraocular lens 9 in a predetermined and unchanging relative axial (and also lateral) position and, as will be explained in more detail below, at the desired angular position relative to the visual axis. Expressed differently, the definition of the cut surfaces 8 is adapted to the individual requirements of the patient and the intraocular lens 9 to be inserted.

In the embodiment of FIG. 1, the cut surfaces 8 are designed and implemented in such a way that the accommodation space 6d is lenticular, and the intraocular lens 9 consists exclusively of the dimensionally stable lens body 9a, which is anchored in sealing fashion in the fastening region 6f embodied as an undercut 12. In the region of the pupil 7, the accommodation space 6d in this case comprises an opening both in the anterior capsular membrane 6a and in the eye lens 6 situated therebelow. Both tissues were left standing only in ring-shaped fashion in an anterior region so that a pocket was formed.

Figure 2:
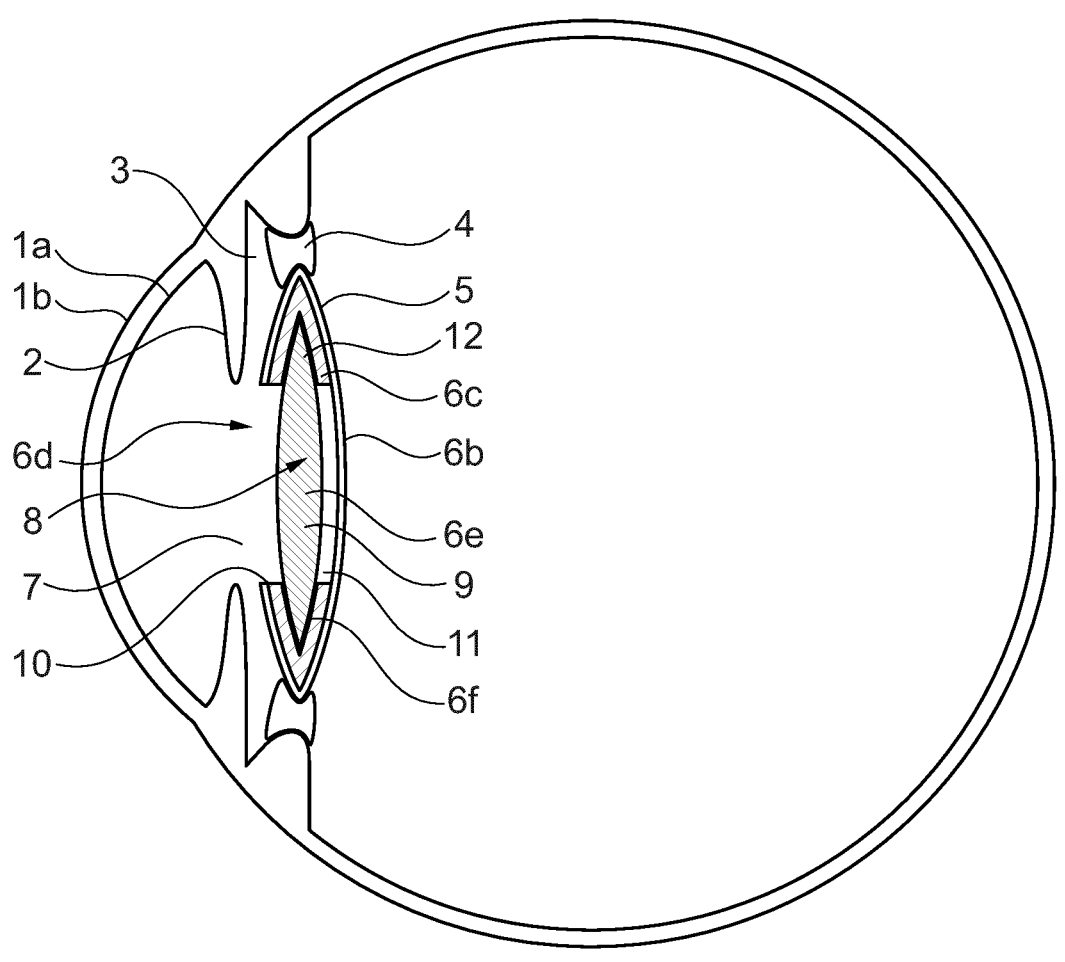

The embodiment in FIG. 2 substantially corresponds to that in FIG. 1 but the cutout 6e is not designed as a depression in this case but as a central channel in the eye lens 6 since eye lens tissue 11 posterior to the intraocular lens 9 was also removed. Hence, the eye lens 6 remained only in two ring-shaped regions, specifically anterior (10) and posterior (6c), and thus forms a fixation pocket for the eye lens 9. The posterior capsular membrane 6b remained in the embodiment shown. This is optional. It could likewise be removed. The seal is also provided in that case.

Figure 3:
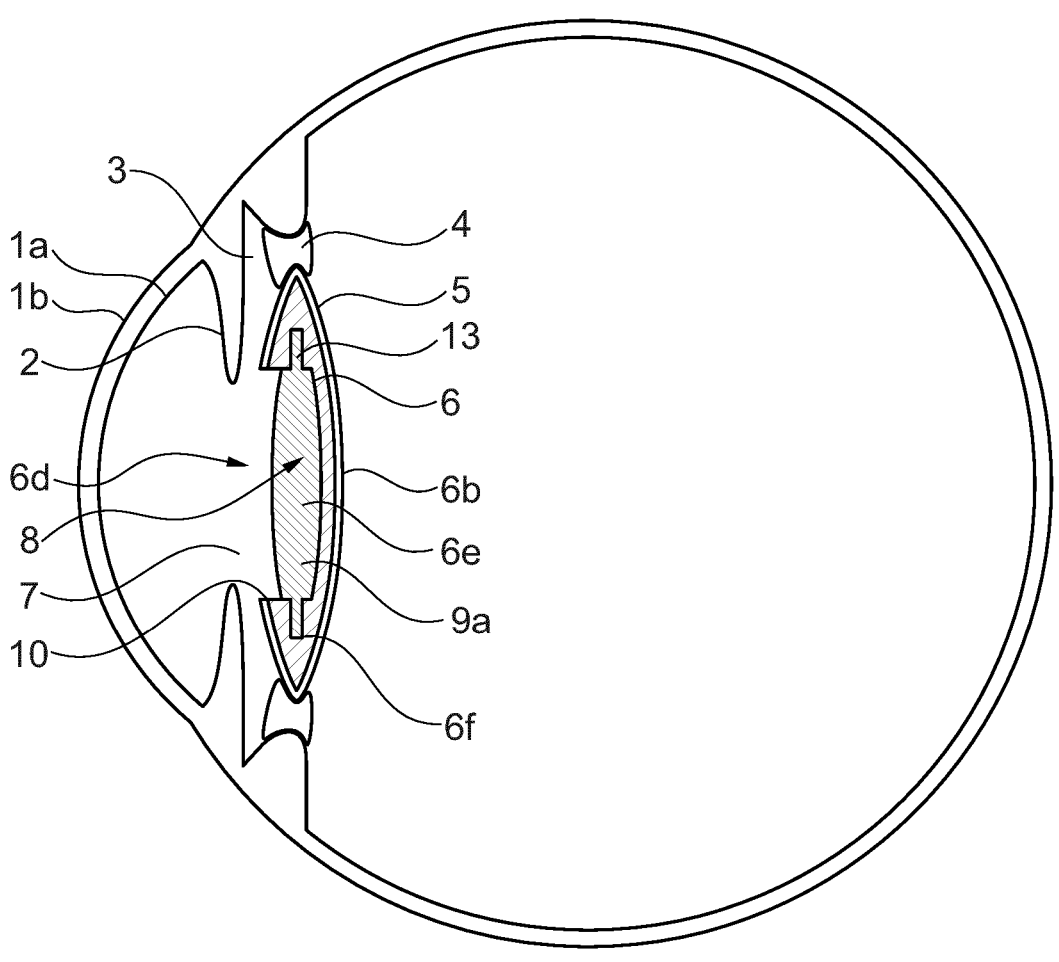
Figure 4:
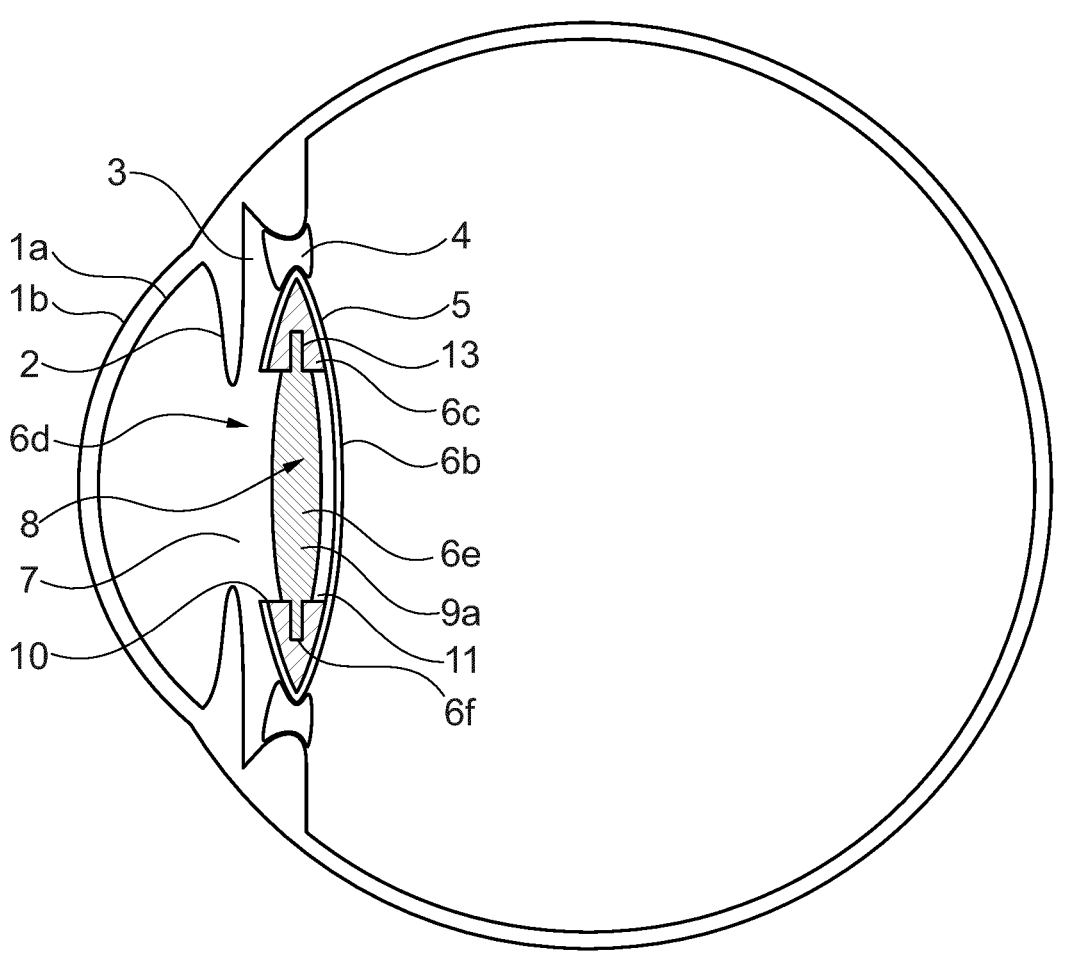

FIG. 3 shows a modification of the embodiment in FIG. 1. In this case, the intraocular lens 9 comprises a lens body 9a which ends peripherally in a snap-lock mechanism. The directly adjacent peripheral fastening region 6f is also formed in the eye lens 6 in addition to the cutout for the dimensionally stable lens body 9a and is formed in a manner adapted to a snap-lock mechanism 13 of the intraocular lens 9. The latter will still be explained in more detail below on the basis of FIGS. 13 and 14. FIG. 4 corresponds to the representation of FIG. 2, but for the snap-lock mechanism of FIG. 3. Leaving the capsular bag 5 standing is also optional in FIG. 4.

Figure 5:
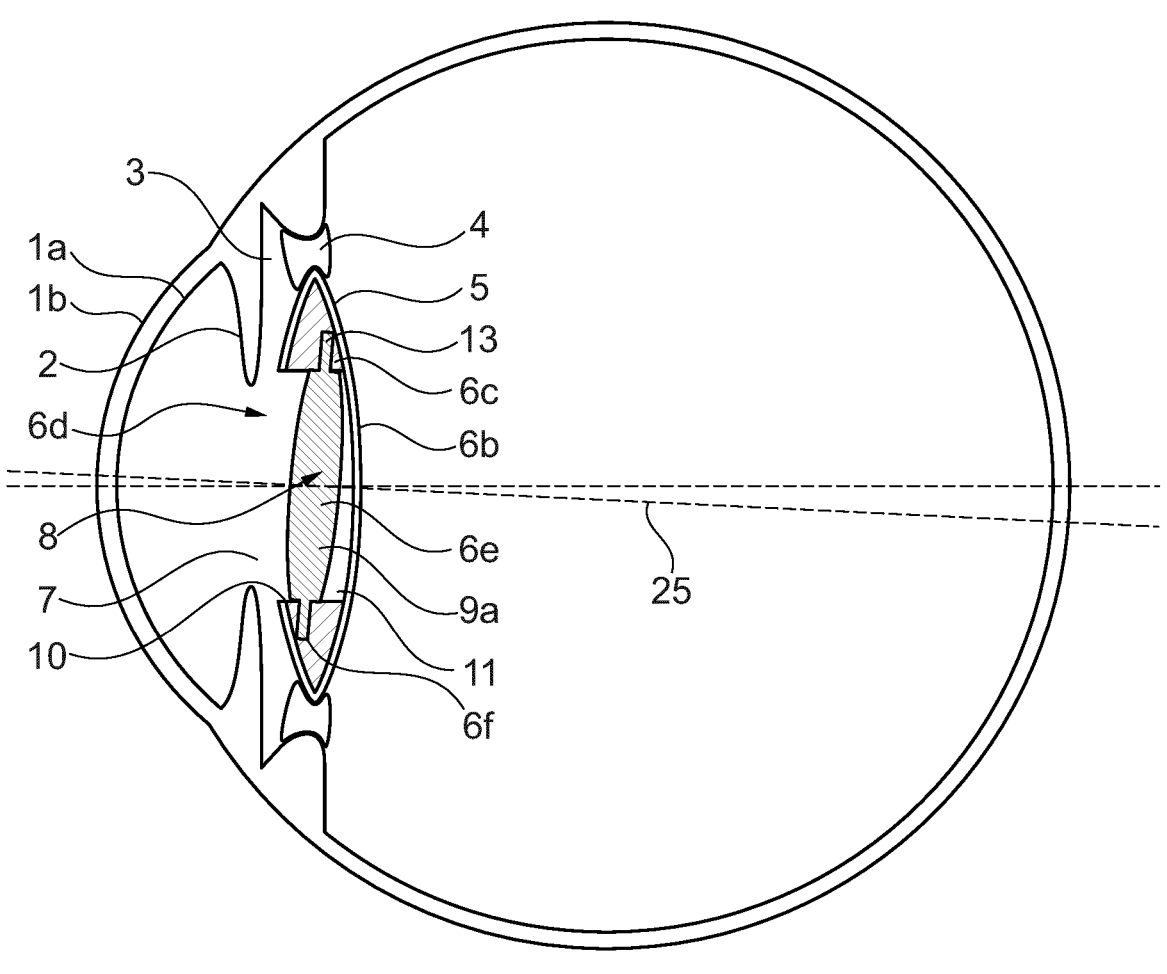

FIG. 5 elucidates the advantages of fastening the intraocular lens 9 with the dimensionally stable lens body 9a in such a way that the latter directly adjoins remaining tissue 6c of the eye lens. Since only a single peripheral fastening region is provided, to accommodate the snap-lock mechanism 13 in this case, it is possible to also arrange the eye lens tilted about a certain angle 25 and thus realize an individualized alignment.

Figure 6:
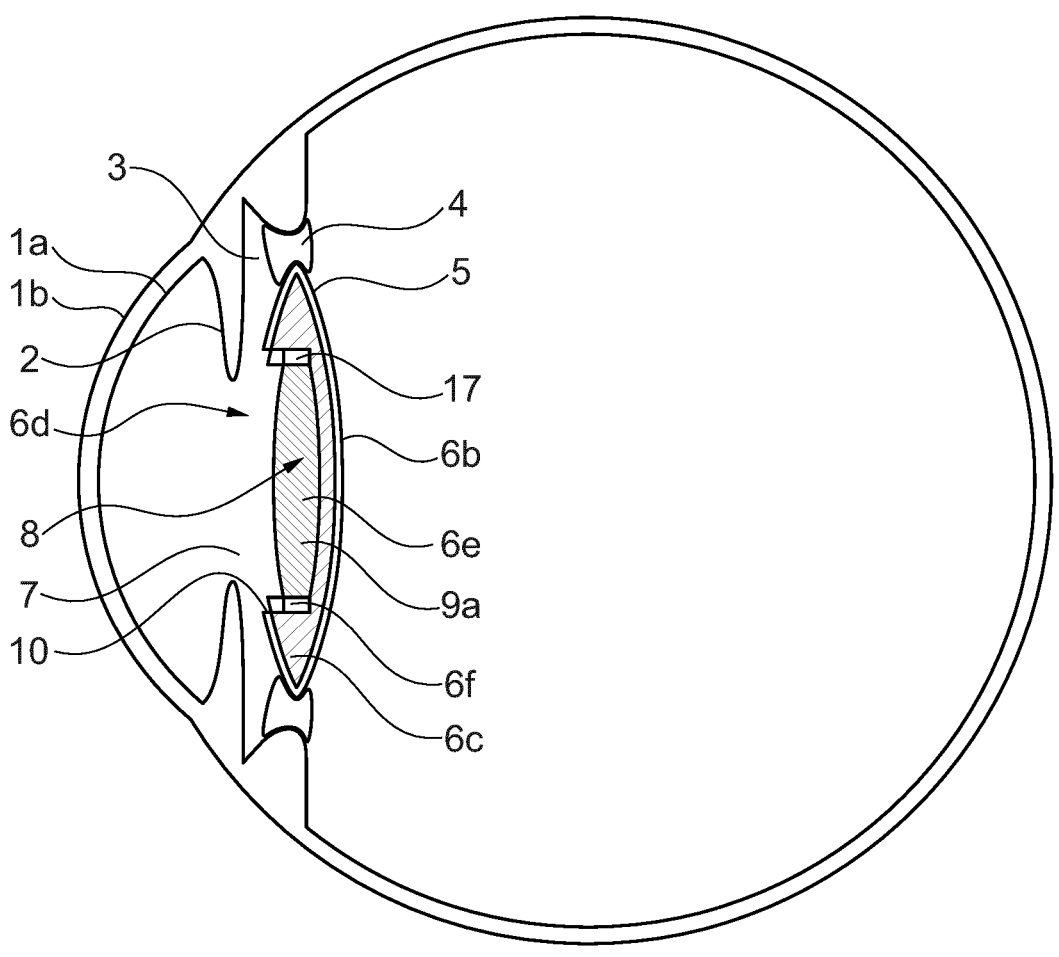
Figure 7:
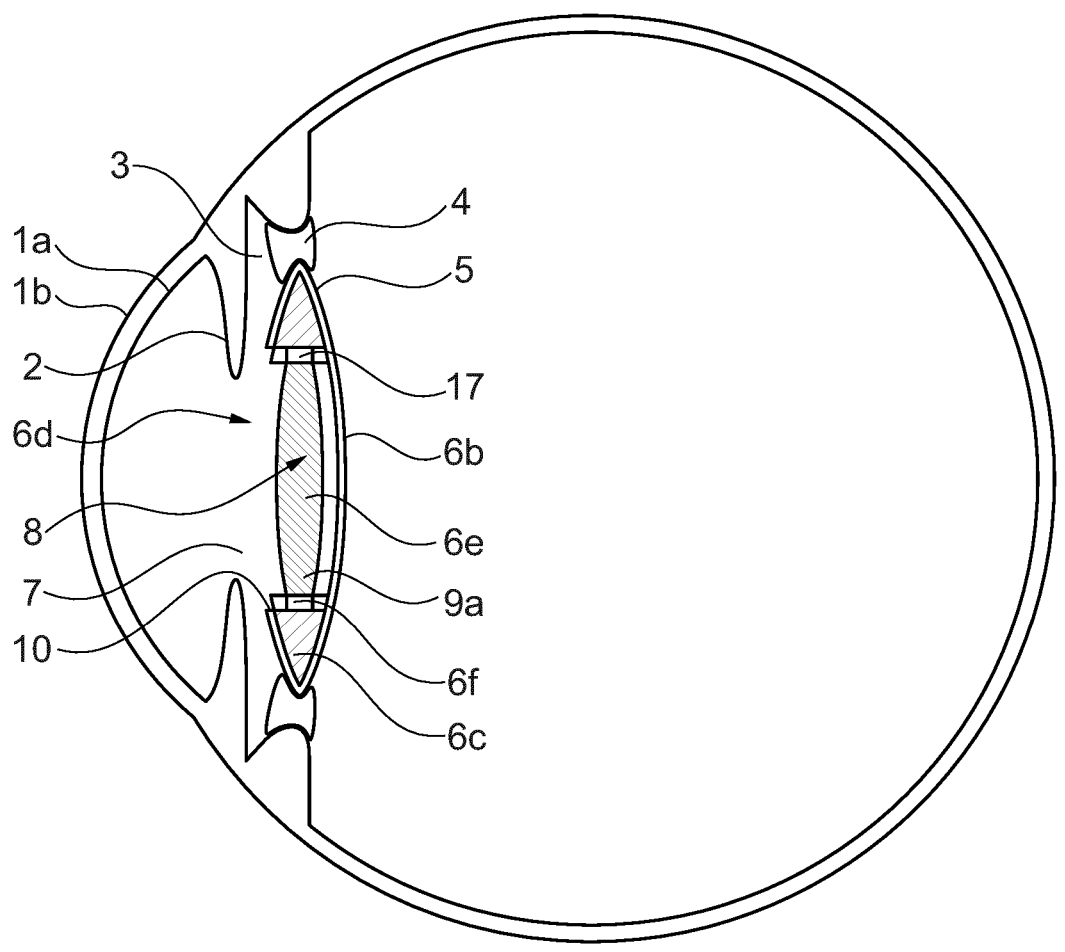

FIG. 6 shows an embodiment similar to FIG. 1, wherein now however the remaining eye lens tissue 6c comprises a thread structure 17, into which a correspondingly fitting thread structure of the intraocular lens 9 is screwed. The residual thickness of the eye lens 6 left posterior ensures that the relative axial position of the intraocular lens 9 is precisely specified when screwing the intraocular lens 9 into the thread structure 17. This stop is not provided in the embodiment of FIG. 7, giving the surgeon greater degrees of freedom when setting the relative axial position of the intraocular lens consisting only of the lens body 9a with the thread structure. Expediently, the intraocular lens is then fixed by means of an adhesive fastening in the region of the thread structure 17.

Figure 8:
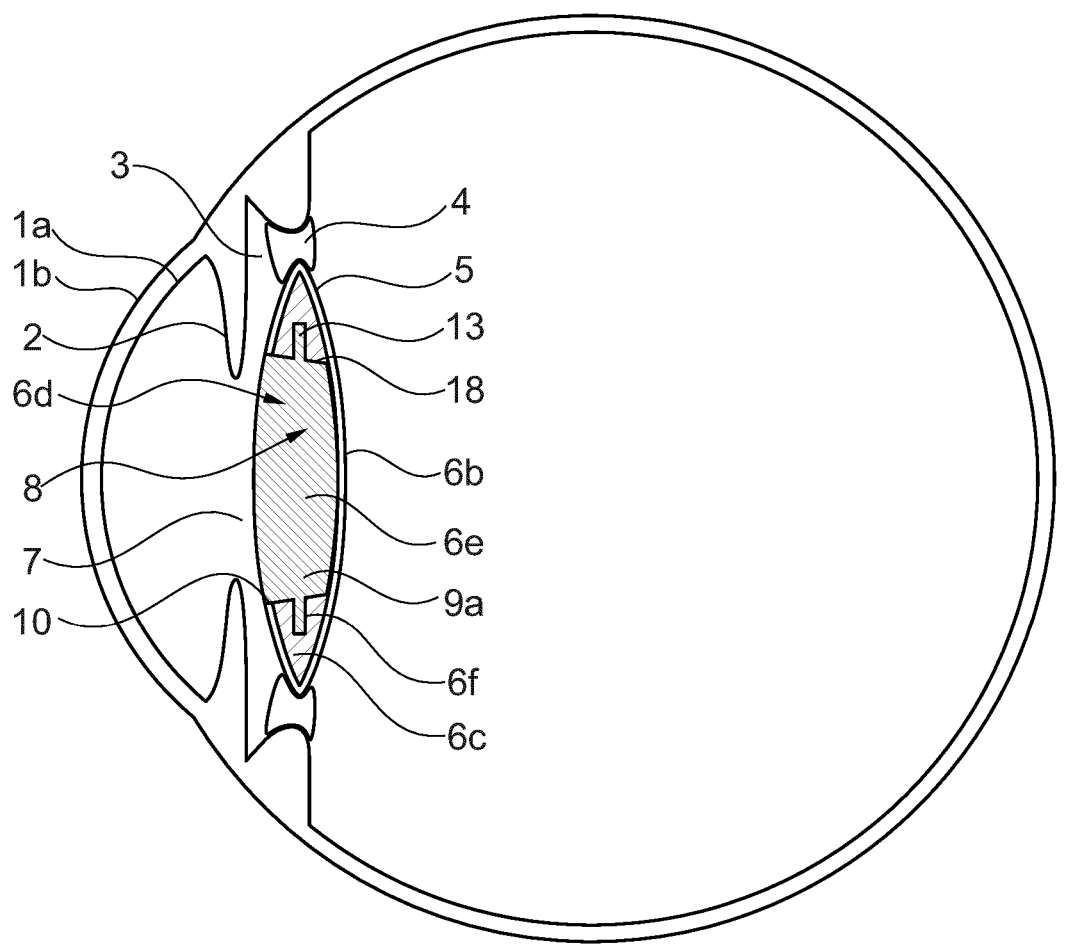
Figure 9:
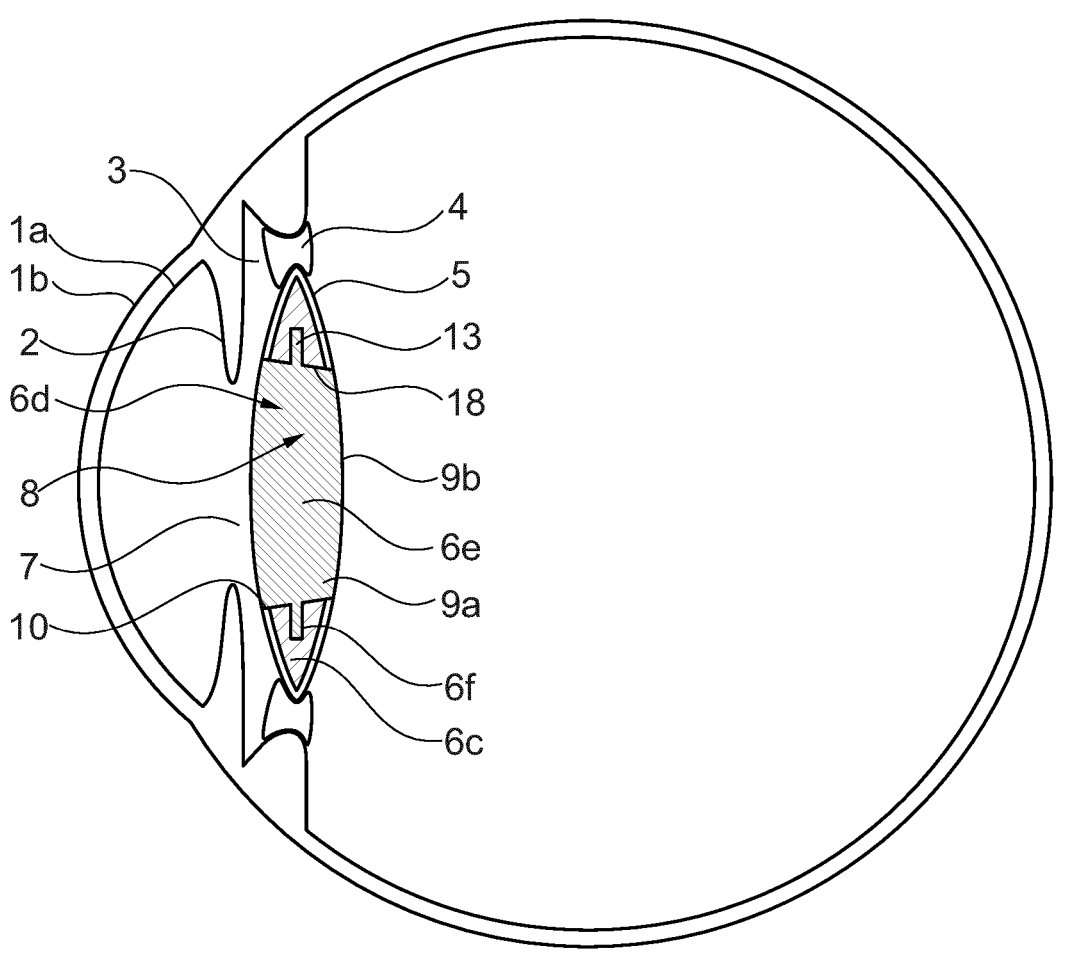

FIG. 8 shows an embodiment similar to that in FIGS. 4 and 5. However, the intraocular lens 9 in this case is additionally provided with a conical edge at the edge of the lens body 9a, said conical edge tapering in the posterior direction, that is to say toward the retina. The remaining tissue 6c of the eye lens 6 is formed with a corresponding conical edge 18 as a shoulder which precisely defines the relative axial position of the lens body 9a when inserting the eye lens with snap-lock technology. From this, the structure in FIG. 9 only differs in that the capsular bag, that is to say the capsular membrane, is also removed posterior to the lens body 9a, that is to say a posterior lens body surface 9b is exposed. Nevertheless, the aforementioned seal is also present here.

Figure 10:
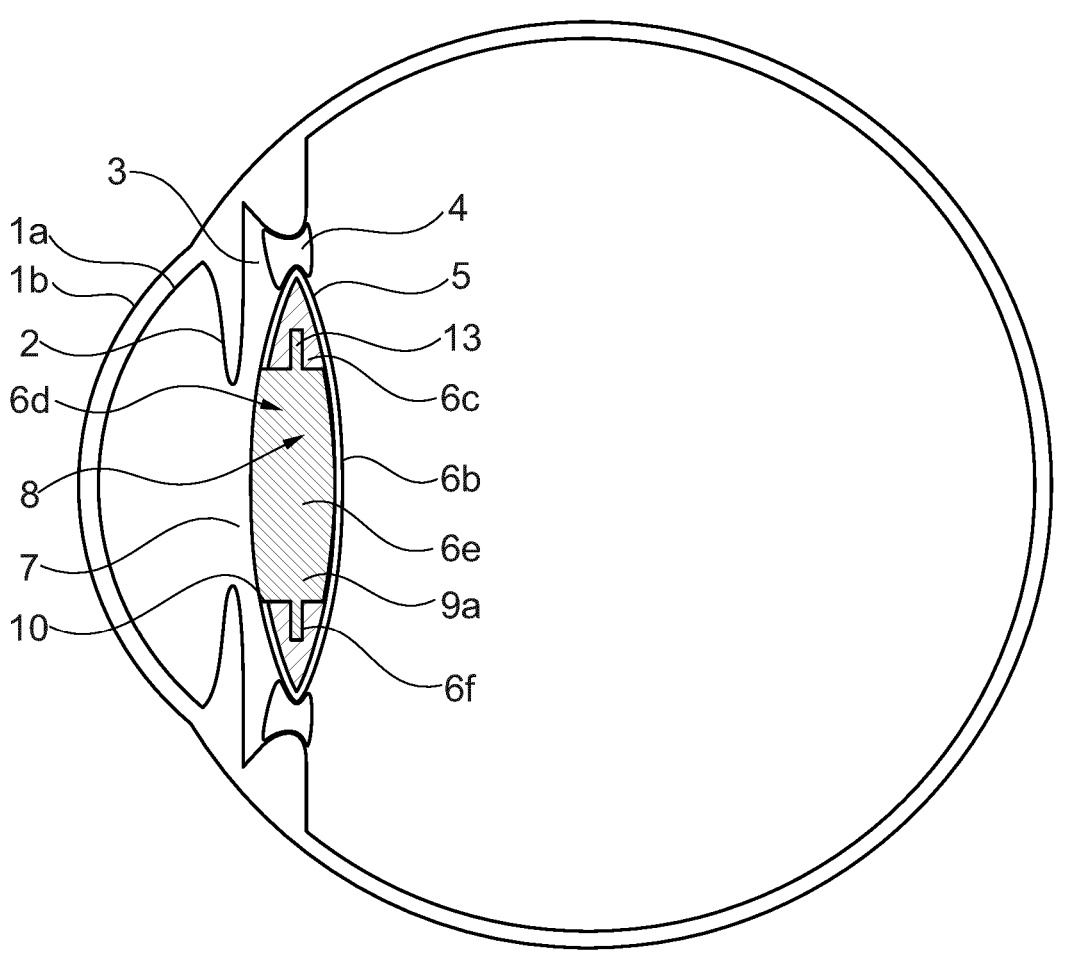
Figure 11:
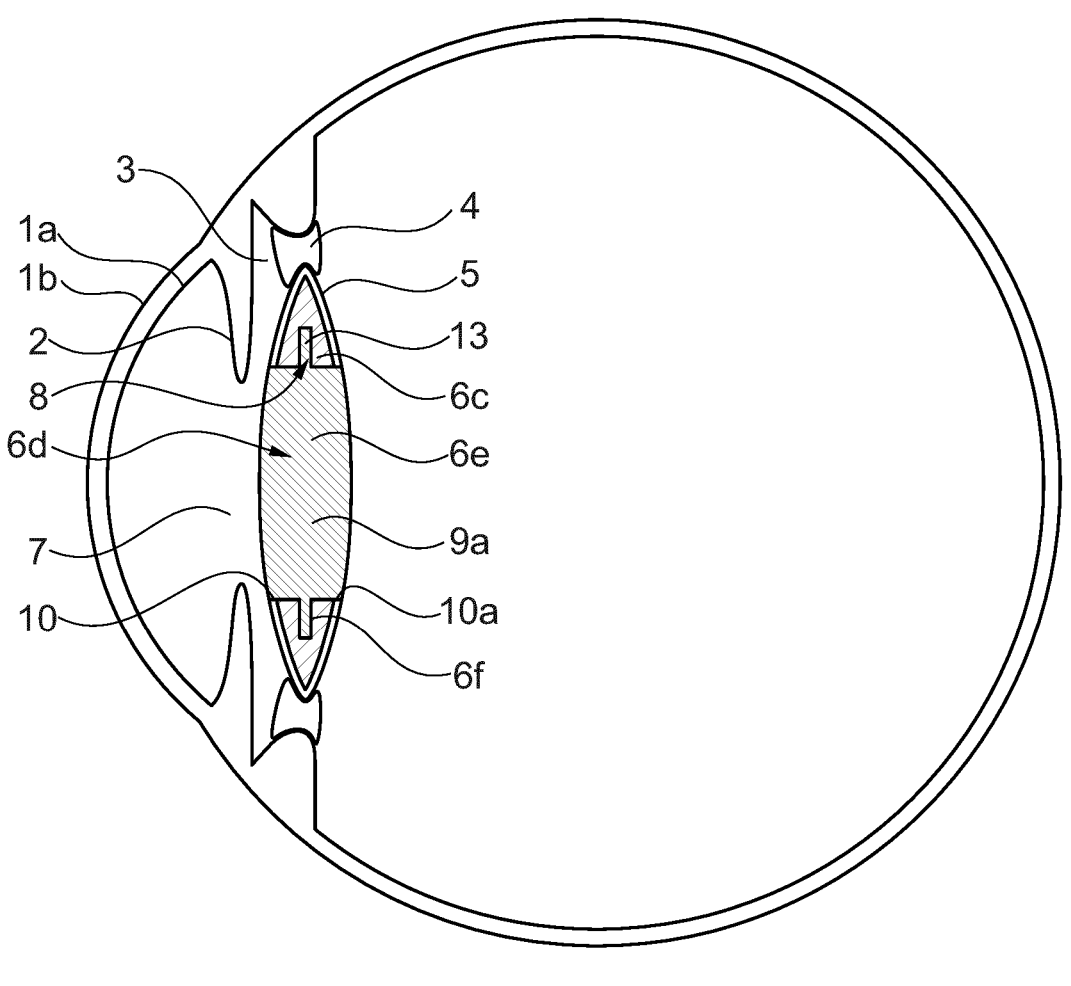

FIGS. 10 and 11 elucidate that the lens body 9a may also be embodied in such a way that it forms a smooth continuation of the anterior capsular membrane on the front side. Hence, no corners arise on the delimiting surface to the anterior chamber, which may be advantageous from a biological point of view. Naturally, this realization can be realized both with an unopened posterior capsular bag 6b (FIG. 10) and with an opened anterior capsular bag and a correspondingly exposed back side of the lens body 9a (FIG. 11). Since only the curvature of its axial boundaries is important in respect of the optical power of the lens body 9a, an increase in the central thickness is unproblematic for optical reasons.

Figure 12:
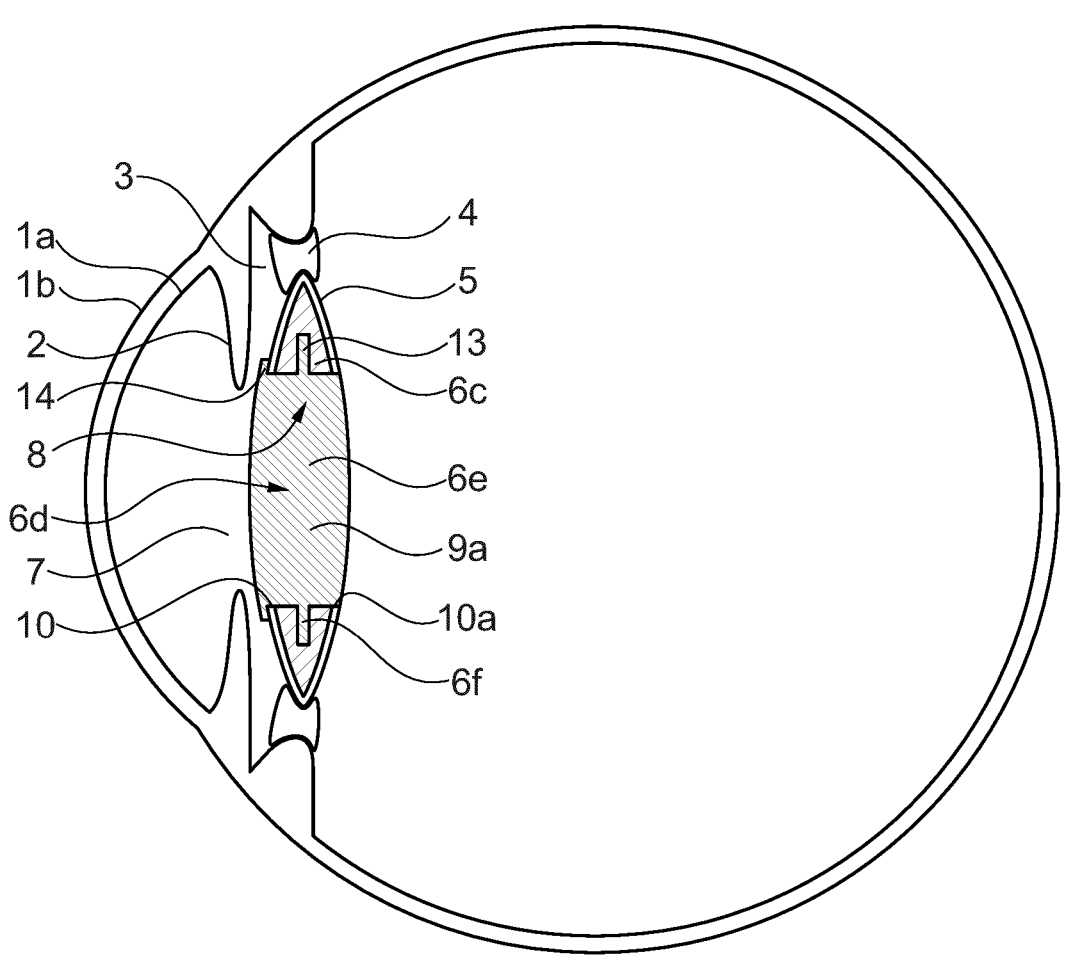

FIG. 12 finally shows a development with a protruding edge 14 on the front side of the lens body 9a. This improves the seal between anterior chamber and posterior chamber. The seal maintains the separation of vitreous humor and anterior chamber, present in the natural eye, even post surgery and independently of the capsular membrane. This is realized in all embodiments of FIGS. 1 to 12.

Figure 13:
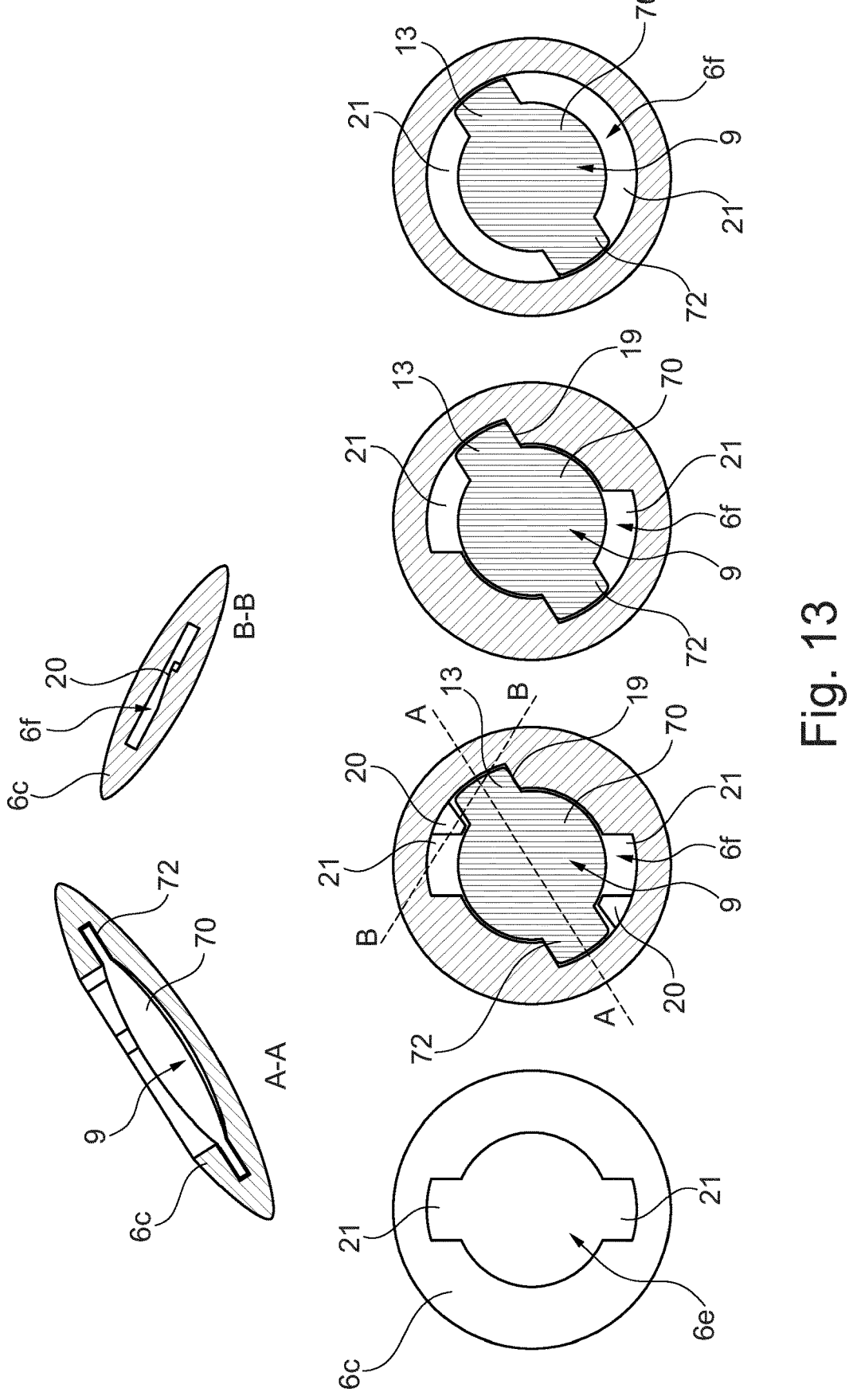
FIG. 13 shows a sectional representation and four plan views of an eye lens, into which an intraocular lens with snap-lock technology is being inserted.

FIG. 13 elucidates the snap-lock technique, used in embodiments, for fastening the intraocular lens 9 in the remaining tissue 6c of the eye lens 6. In this case, the upper representations in FIG. 13 show a sectional representation along the lines A-A and B-B, respectively. The snap-lock mechanism serves to fix the intraocular lens 9 in the remaining tissue 6c of the prepared natural eye lens. To this end, a three-dimensional pocket is cut and the tissue of the eye lens 6 that is not required is comminuted and removed. The pocket comprises a suitable entry window 21, through which wings 13 of the intraocular lens 9 can be inserted. By rotation of the intraocular lens 9, the wings 13 are guided posteriorly by existing lens material and the lens 9 is consequently fixed in its relative axial and rotational position. In this case, the intraocular lens 9 is rotated until the wings 13 are incident on a mechanical stop surface 19. This surface defines the correct rotational position and hence the correct axis position for correcting the astigmatism in the case of a toric intraocular lens. To prevent an unwanted back rotation of the intraocular lens 9, at least one of the wings 13 is optionally guided over a latch 20. To insert the wing or wings 13, the entry window 21 through which the wing can be inserted into the peripheral fastening region 6f before the intraocular lens 9 is rotated is implemented for each wing 13 in the three-dimensionally prepared pocket. In this way, the intraocular lens 9 is fixed in a predetermined relative axial and also rotational position with its lens body 70 which provides the optical power of the intraocular lens, the fixation being brought about by virtue of the wings 13 for the snap-lock fastening being formed at the edge 72 of the lens body 70. The intraocular lens 9 has no haptics, that is to say no attached arms, which fasten the otherwise freely suspended intraocular lens.

In the four lower figures, FIG. 13 shows plan views of the accommodation space 6d created in the tissue 6c of the natural eye lens (first representation from the left), the state with the lens body anchored in the accommodation space in a sectional plane corresponding to the central plane of the lens (second representation from the left), a section like the second representation from the left but for a variant without latch 20 (third representation from the left), and a representation in the same sectional plane for a variant without end stop and without latching position (right representation in FIG. 13).

Figure 14:
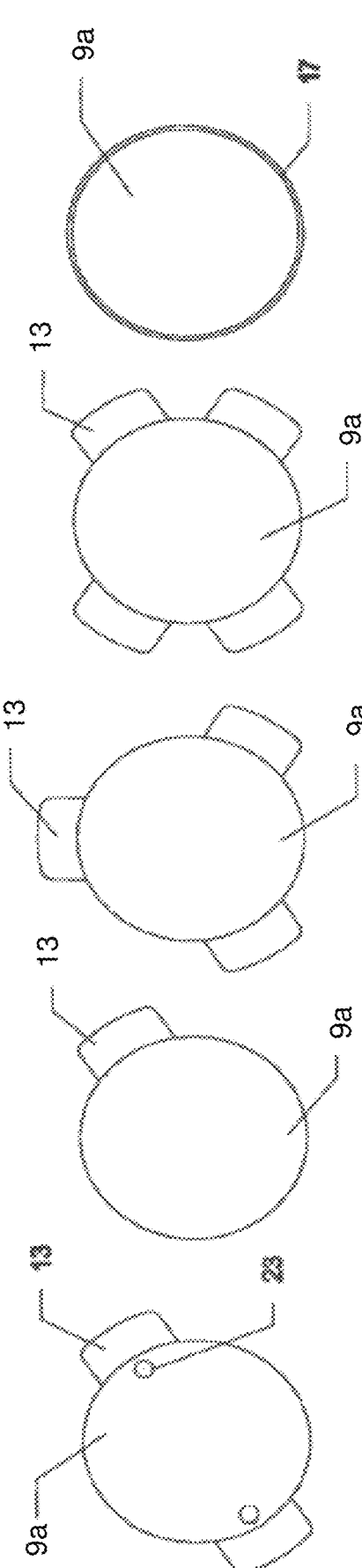
FIG. 14 shows four different options for realizing the intraocular lens to be inserted using the snap-lock technique and an intraocular lens with a thread structure for fastening in the eye lens.

FIG. 14 schematically shows next to one another five representations of different realizations of the intraocular lens for snap-lock technology. In the left representation, the intraocular lens has two wings for snap-lock fastening. Additionally, a bore 23 is shown in exemplary fashion; it can be used to position and rotate the intraocular lens 9. The wings 13 are located outside of an optical zone of the intraocular lens. Only one wing 13 is provided in the second representation from the left. Three and four wings 13 are formed on the lens body 9a in the central representation and in the fourth representation from the left, respectively. Finally, the right-hand representation relates to a lens body 9a with a thread structure 17 for the embodiments in FIGS. 6 and 7.

Figure 15:
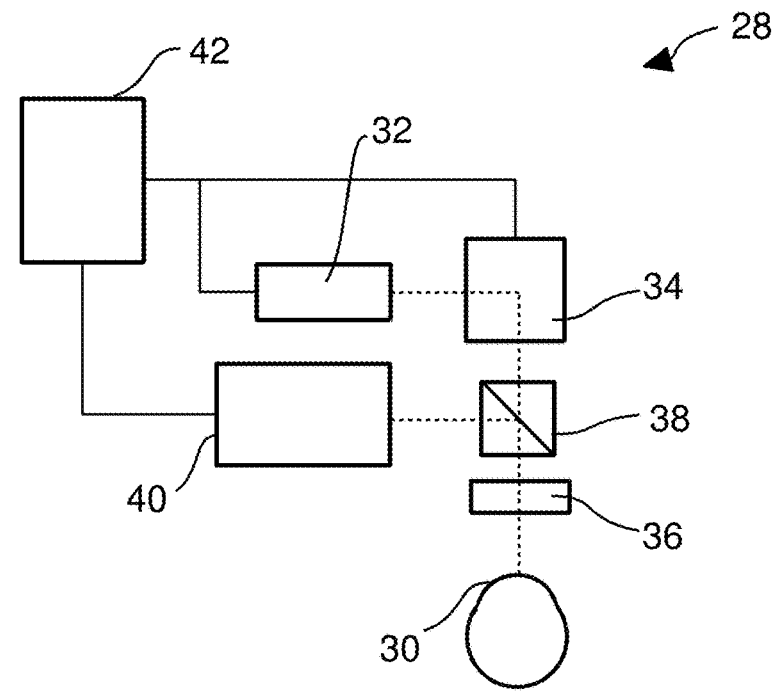
FIG. 15 shows a schematic representation of an apparatus for preparing the eye lens.

FIG. 15 schematically shows a treatment apparatus 28 for preparing the eye lens 6 in an eye 30. The apparatus 28 comprises an fs short pulse laser, as is known from the prior art for generating optical breakdown and for separating tissue in the eye lens and in the capsular bag. The radiation of the laser 32 is focused via a scanning mechanism 34 for the 3-D adjustment of the relative focal position in the eye 30 and via an optical unit 38 into the eye lens 6 or capsular bag in such a way that tissue can be separated there and the eye lens 6 can be prepared as described above. In the process, the radiation also runs through a beam splitter 38, where the beam path of a measuring apparatus 40, for example an optical coherence tomography device, a wavefront sensor, a slit lamp and/or a Scheimpflug camera, is coupled in. Laser 32, scanner 34 and the measuring apparatus 40 are connected to a controller 42 which receives the measurement data from the measuring device 40, which determines the relative position of the eye structures, in particular of the eye lens and capsular bag in the eye 30, therefrom, which defines a shot pattern for the fs short pulse laser 32 and which controls the three-dimensional beam deflection 34 (within the scope of which the objective lens 36 may optionally also be involved) in such a way that the cut surfaces for the desired generation of the accommodation space with the cutout for the dimensionally stable lens body 9a of the intraocular lens 9 and the peripheral fastening region 6f for fixing the lens body are correspondingly separated from the remaining eye tissue 6c so that following the removal of this separated tissue the corresponding structures are prepared in order to be able to insert the interlenticular intraocular lens 9. The optical connection of the measuring device 40 can be chosen freely and need not necessarily run through the optical unit 38. In other embodiments, the measuring apparatus 40 (which precisely measures and also references the eye) is coupled externally, and internally, to the beam path, for example, there being a simple registration device which retrieves the referencing (structures) determined by the measuring apparatus.

Figure 16:
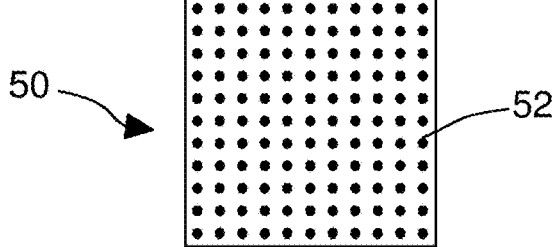
FIG. 16 shows a schematic representation of a pattern of focal locations for generating a cut surface.

FIG. 16 schematically shows a pattern 50 of locations 52 for the focus, as brought about by the scanning mechanism 34 under control of the controller 42. A cut surface 8, which is planar and square purely by way of example in FIG. 16, is generated by a suitable arrangement of the locations 52 in the pattern 50.

Figure 17:
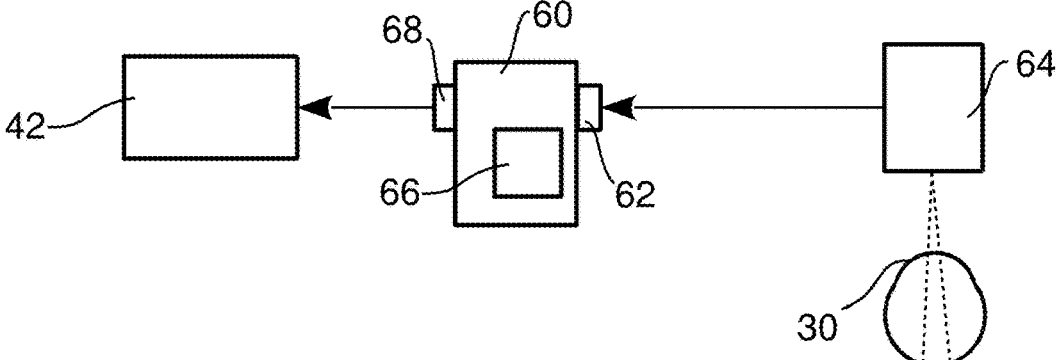
FIG. 17 shows a schematic representation of an apparatus for planning a surgical intervention on the human eye lens.

FIG. 17 shows an apparatus for planning the lens-surgical intervention. The apparatus is substantially formed by a planning station 60 which has an input interface 62 in order to obtain measurement data, originating from a measuring device 64, about the eye 30. By way of example, this may be an optical coherence tomography device, which detects the eye structure and, in particular, images the eye lens with sufficient accuracy. The data supplied at the input interface 62 are then used by a computer device 66 to define the cut surface. To this end, a surgeon may input appropriate entries on the planning station 60 in order to define the cut surfaces 8 accordingly. Furthermore, a database may already be available in the planning station 60 and contain specifications, especially geometric and dimensional specifications, regarding possible intraocular lenses 9. As a result of the implemented method, the planning station 60 outputs control data for the control device 42 at an output interface 68.

The invention claimed is:

1. An apparatus for carrying out lens surgery on a human eye, comprising:
   a laser device for separating tissue of an eye lens of the human eye and a capsular bag of the human eye in a focus of pulsed laser radiation,
   a focus positioning device for setting and adjusting a location of the focus, a registration device for referencing the relative position of the location of the focus in relation to the relative position of eye structures comprising the eye lens and the capsular bag, and a control device which reads data from the registration device and which controls the focus positioning device and which is designed to specify a pattern for the focus to the focus positioning device, said pattern forming cut surfaces which separate tissue layers in the eye lens for purposes of generating an accommodation space in the eye lens for receiving an intralenticular intraocular lens, wherein the accommodation space comprises a cutout, open toward an anterior chamber of the eye, for inserting a dimensionally stable lens body of the intraocular lens and realizing at least one of the following features:
   a) the accommodation space comprises a peripheral fastening region for fixing the lens body at a single, predetermined, axial position,
   b) the accommodation space comprises a peripheral fastening region for fixing the lens body, the accommodation space and the fastening region being designed to receive the intraocular lens in sealing fashion so that the anterior chamber of the eye is separated in sealed fashion from rearward portions of the eye, and
   c) a continuous posterior layer of tissue of the eye lens remains posterior to the cutout for the lens body, wherein the cut surfaces form the accommodation space, to completely surround the intraocular lens with tissue of the eye lens both posterior and anterior in a peripheral ring region.

2. The apparatus as claimed in claim 1, further comprising a measuring apparatus for generating image data of eye structures comprising the eye lens and the capsular bag, the image data forming a basis for defining the cut surfaces.

3. The apparatus as claimed in claim 1, wherein the cut surfaces anterior to the accommodation space leave an anterior layer of tissue of the eye lens only in a peripheral eye lens region and the cutout inside of this peripheral eye lens region is open toward the anterior chamber.

4. The apparatus as claimed in claim 1, wherein the cut surfaces form the accommodation space as an anteriorly open pocket for the intraocular lens which only consists of the lens body, and the peripheral fastening region, when considered axially, is in the form of an outwardly tapering undercut.

5. The apparatus as claimed in claim 1, wherein the cut surfaces form the peripheral fastening region for snap-lock fastening.

6. The apparatus as claimed in claim 1, wherein the cut surfaces provide the peripheral fastening region with a thread structure.

7. The apparatus as claimed in claim 1, wherein the cut surfaces form the peripheral fastening region as an annular groove.

8. The apparatus as claimed in claim 1, wherein the cut surfaces form the peripheral fastening region with at least one, conical shoulder for contact with the lens body of the intraocular lens.

9. The apparatus as claimed in claim 1, wherein the cut surfaces are formed for the lens body which is dimensionally stable and which has an optical power to replace the natural eye lens of the human eye.

10. An apparatus for carrying out lens surgery on the human eye, comprising:

a laser device for separating tissue of an eye lens of the human eye and a capsular bag of the human eye in a focus of pulsed laser radiation, a focus positioning device for setting and adjusting a location of the focus, a registration device for referencing the relative position of the location of the focus in relation to a relative position of eye structures comprising the eye lens and the capsular bag, and a control device which reads data from the registration device and which controls the focus positioning device and which is designed to specify a pattern for the focus to the focus positioning device, said pattern forming cut surfaces which separate tissue layers in the eye lens for purposes of generating an accommodation space for an intralenticular intraocular lens, wherein the accommodation space comprising a cutout for inserting a dimensionally stable lens body of the intraocular lens and realizing at least one of the following features:

a) the accommodation space comprises a peripheral fastening region for fixing the lens body at a single, predetermined, axial position, b) the accommodation space comprises a peripheral fastening region for fixing the lens body, the accommodation space and the fastening region being designed to receive the intraocular lens in sealing fashion so that an anterior chamber of the eye is separated in sealed fashion from rearward portions of the eye, and c) a continuous posterior layer of tissue of the eye lens remains posterior to the cutout for the lens body, wherein the cut surfaces form the accommodation space, to completely surround the intraocular lens with tissue of the eye lens both posterior and anterior in a peripheral ring region.

11. A method for lens surgery on the human eye, comprising the steps of:

providing an intralenticular intraocular lens comprising a lens body, generating cut surfaces in an eye lens of the human eye, the cut surfaces separating tissue layers in the eye lens for purposes of generating an accommodation space for the intralenticular intraocular lens and the accommodation space comprising a cutout, open toward an anterior chamber, for a lens body of the intraocular lens and realizing at least one of the following features:

a) the accommodation space comprises a peripheral fastening region for fixing the lens body at a single, predetermined, axial position, b) the accommodation space comprises a peripheral fastening region for fixing the lens body, the accommodation space and the fastening region being designed to receive the intraocular lens in sealing fashion so that the anterior chamber of the eye is separated in sealed fashion from rearward portions of the eye, and c) a continuous posterior layer of tissue of the eye lens remains posterior to the cutout for the lens body, and removing a volume delimited by the cut surfaces, wherein the cut surfaces form the accommodation space, to completely surround the intraocular lens with tissue of the eye lens both posterior and anterior in a peripheral ring region.

12. A method for lens surgery on the human eye, comprising the steps of:

providing an intralenticular intraocular lens comprising a lens body, generating cut surfaces in an eye lens of the human eye, the cut surfaces separating tissue layers in the eye lens for the purposes of generating an accommodation space for the intralenticular intraocular lens and the accommodation space comprising a cutout for a lens body of the intraocular lens and realizing at least one of the following features:

a) the accommodation space comprises a peripheral fastening region for fixing the lens body at a single, predetermined, axial position, b) the accommodation space comprises a peripheral fastening region for fixing the lens body, the accommodation space and the fastening region being designed to receive the intraocular lens in sealing fashion so that an anterior chamber of the eye is separated in sealed fashion from rearward portions of the eye, and c) a continuous posterior layer of tissue of the eye lens remains posterior to the cutout for the lens body, and removing a volume delimited by the cut surfaces, wherein the cut surfaces form the accommodation space, to completely surround the intraocular lens with tissue of the eye lens both posterior and anterior in a peripheral ring region.

13. The method as claimed in claim 12, further comprising the steps of:

gathering a measurement data which indicate a relative position of eye structures comprising an eye lens of the human eye and a capsular bag-of the human eye, defining the cut surfaces in the eye lens and determining a pattern of locations of a focus of pulsed laser radiation, the locations being located on the defined cut surfaces, and generating data representing the pattern of locations for an apparatus that emits the pulsed laser radiation to generate the cut surfaces in the eye lens.

14. The method as claimed in claim 13, further comprising insertion of the intraocular lens into the accommodation space.

15. The method as claimed in claim 13, wherein the cut surfaces are formed such that an anterior layer of tissue of the eye lens remains anterior to the cutout, said anterior layer of tissue being continuous apart from an access incision which leads to the cutout and penetrates the tissue of the eye lens and capsular bag.

* * * * *